United States Patent [19]

Hendrick et al.

[11] Patent Number: 5,065,106
[45] Date of Patent: Nov. 12, 1991

[54] APPARATUS AND METHOD FOR ANALYZING DIELECTRIC PROPERTIES USING A SINGLE SURFACE ELECTRODE AND FORCE MONITORING AND ADJUSTING

[75] Inventors: Kendall Hendrick, Landenberg, Pa.; John R. Reader, Jr., Newark, Del.

[73] Assignee: TA Instruments, Inc., New Castle, Del.

[21] Appl. No.: 660,169

[22] Filed: Feb. 25, 1991

Related U.S. Application Data

[63] Continuation of Ser. No. 380,545, Jul. 12, 1989, abandoned, which is a continuation-in-part of Ser. No. 206,092, Jun. 13, 1988, Pat. No. 4,855,667.

[51] Int. Cl.$^5$ .............................................. G01R 27/26
[52] U.S. Cl. ................................... 324/663; 324/684; 324/687
[58] Field of Search ............... 324/658, 661, 662, 663, 324/671, 683, 685, 686, 687, 688, 690, 158 P; 364/476, 477; 425/143, 149; 219/10.73, 528

[56] References Cited

U.S. PATENT DOCUMENTS

| | | | |
|---|---|---|---|
| 3,488,758 | 1/1970 | Benson et al. | 324/61 |
| 3,613,454 | 10/1971 | McFadin | 73/362 |
| 3,712,125 | 1/1973 | Meyer | 73/90 |
| 3,809,973 | 5/1974 | Hurley | 317/258 |
| 3,872,360 | 3/1975 | Sheard | 317/258 |
| 3,986,109 | 10/1976 | Poduje | 324/61 R |
| 3,999,040 | 12/1976 | Ellis | 219/528 X |
| 4,082,906 | 4/1978 | Amin et al. | 428/539 |
| 4,096,758 | 6/1978 | Moore | 73/718 |
| 4,103,275 | 7/1978 | Diehl et al. | 338/25 |
| 4,129,848 | 12/1978 | Frank et al. | 338/308 |
| 4,140,998 | 2/1979 | Bettle | 340/199 |
| 4,186,368 | 1/1980 | White et al. | 338/28 |
| 4,311,549 | 1/1982 | Vercillo | 100/93 P |
| 4,380,484 | 4/1983 | Repik et al. | 219/10.73 |
| 4,387,339 | 6/1983 | Akerblom | 324/207 |
| 4,423,371 | 12/1983 | Senturia et al. | 324/61 R |
| 4,436,438 | 3/1984 | Voznick | 374/165 |
| 4,559,797 | 12/1985 | Raymond | 72/63 |
| 4,625,401 | 12/1986 | Cvijanovich | 29/885 |
| 4,658,212 | 4/1987 | Ozawa et al. | 324/158 P X |
| 4,678,991 | 7/1987 | Schmidt | 324/207 |
| 4,710,550 | 12/1987 | Kranbuehl | 526/60 |
| 4,723,908 | 2/1988 | Kranbuehl | 324/71 P X |
| 4,773,021 | 9/1988 | Harris et al. | 364/476 |

FOREIGN PATENT DOCUMENTS

2187291 9/1987 United Kingdom .

*Primary Examiner*—Jack B. Harvey
*Attorney, Agent, or Firm*—Kirkland & Ellis

[57] ABSTRACT

A parallel plate or single surface dielectric analyzer is disclosed including: a distance sensor for accurately measuring the varying distance between the electrodes, such as a linear voltage differential transformer (LVDT), and apparatus responsive to the distance sensor for positioning the electrodes; a force transducer for measuring the applied force on the sample and apparatus responsive to the force transducer to give a desired force by varying the electrode spacing; disposable electrodes made using thick film technology composed of a ceramic substrate with a conductor adhered to its surface; and a temperature sensor built into one of the electrodes such as a platinum ring adhered to the surface of one of the electrodes and apparatus to measure the resistance across the platinum ring.

9 Claims, 13 Drawing Sheets

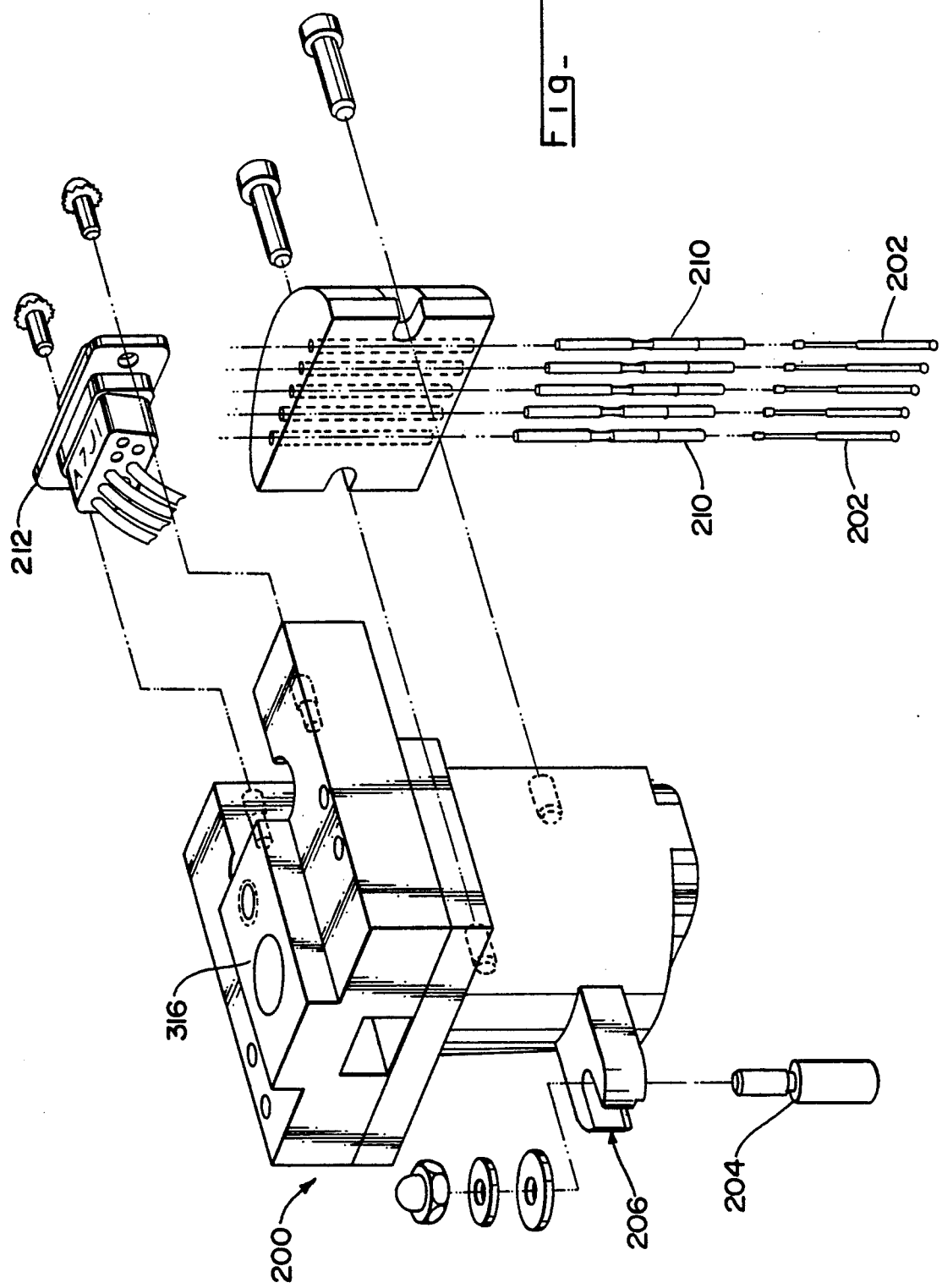

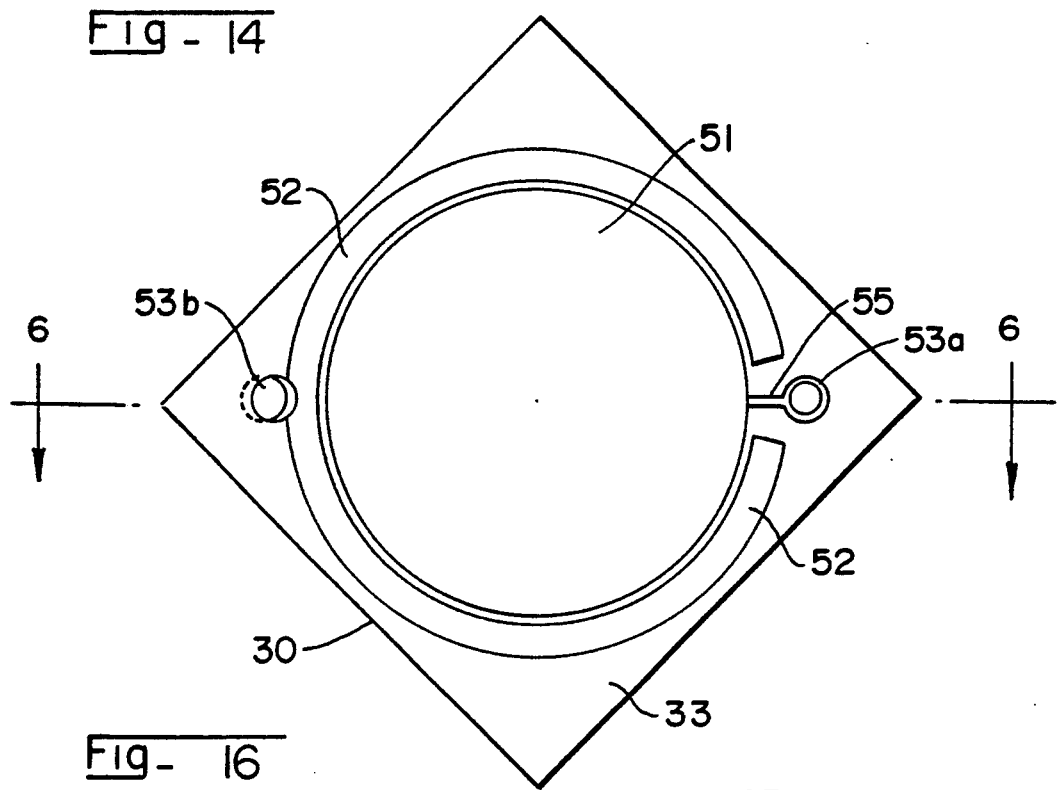
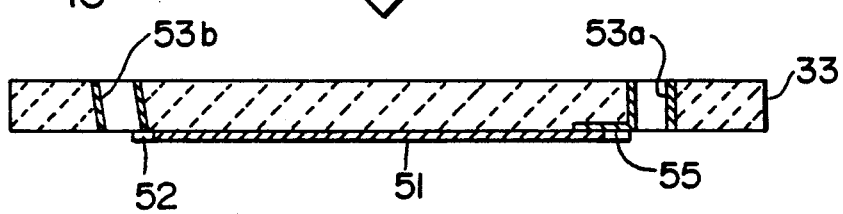
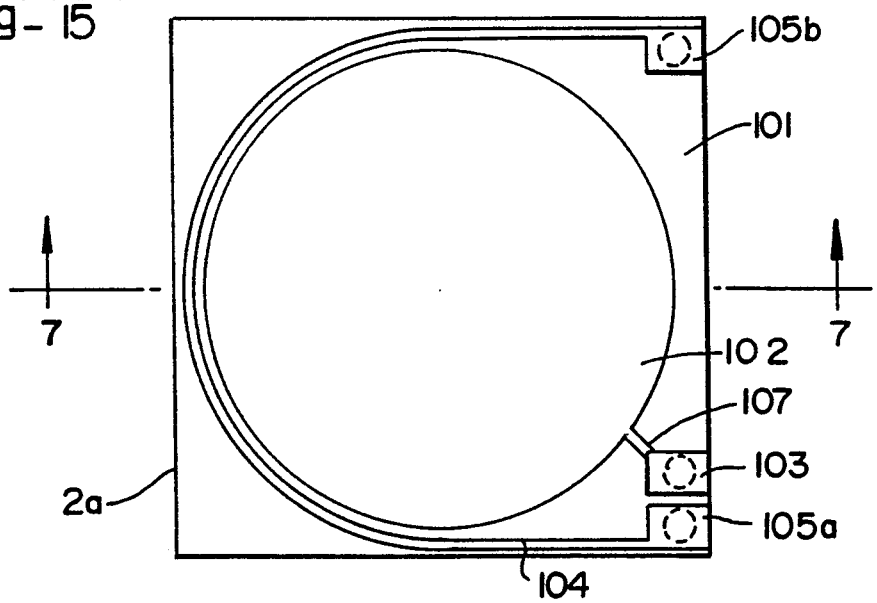
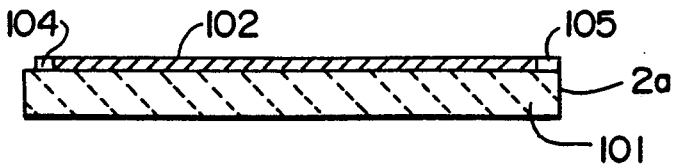

APPARATUS AND METHOD FOR ANALYZING DIELECTRIC PROPERTIES USING A SINGLE SURFACE ELECTRODE AND FORCE MONITORING AND ADJUSTING

This is a continuation of co-pending application Ser. No. 07/380,545, filed on July 12, 1989, now abandoned, which is a continuation-in-part of U.S. application Ser. No. 07/206,092, filed June 13, 1988, now issued as U.S. Pat. No. 4,855,667.

BACKGROUND OF THE INVENTION

This invention relates to an apparatus for analyzing the dielectric properties of a sample by the use of parallel plate electrodes or single surface interdigitated pectinate electrodes.

It is well known that by measuring the dielectric properties of a sample as a function of temperature, valuable information can be gained concerning the physical and chemical properties of the sample. For many years such measurements have been made by placing a sample between parallel plate electrodes, applying an electrical signal to one of the electrodes (i.e. the excitation electrode) and measuring the electrical signal from the other electrode (i.e. the response electrode). The following equation is used:

$$C = e_o e' A / d$$

where
- C = Capacitance
- $e_o$ = Permittivity of Free Space (a constant)
- $e'$ = Permittivity of Sample (being measured)
- A = Area of Parallel Plate Response Electrode
- d = Distance Between the Excitation and Response Electrode Plates By measuring capacitance, the permittivity of the sample ($e'$) can easily be calculated if the area of the parallel plate electrode and the distance between the excitation and response electrodes are known. However, a common dilemma when making these measurements is obtaining an accurate measurement of distance between the plates. This is because most measurements are made as a function of temperature, and the sample changes in dimension as the experiment progresses. However, despite this fact, prior parallel plate dielectric analyzers have usually assumed the distance between the electrodes to be the thickness of the sample at room temperature. Thus, as the material expands or contracts as a function of temperature, the measured values are in error by the factor:

$$\frac{\text{Thickness of the Sample at Measurement Temperature}}{\text{Thickness of the Sample at Room Temperature}}$$

In some instances this error is compensated by allowing for the coefficient of thermal expansion (CTE) of the material (assuming it is known with some accuracy). But this is not an accurate correction since the CTE changes as a material goes through its glass transition. The CTE also assumes zero force on the sample which is not practical when making dielectric measurements on solid samples.

All known instruments either apply a constant force to a sample initially and run the experiment in that mode (constant force), or set a plate spacing and let it remain constant during an experiment (constant distance). In the constant force mode, at elevated temperatures, when the sample melts, the two plates come together, short circuit, and the experiment is prematurely terminated. In the constant distance mode, if the sample melts, contact with the top plate is lost, and once again the experiment is prematurely terminated.

Another significant practical problem with conventional parallel plate dielectric analyzers arises because current analyzers use either steel or gold plated metallic plates. After a sample has passed its glass transition $T_G$ (point of interest), it begins to flow, and as it cools it can adhere to the highly-polished, precision-machined plates. Many times plates must be removed from the instrument to scrape samples off. The plates must then be reground to ensure parallelism for the next experiment. This can be a costly and time-consuming operation. One popular alternative is to use a thin release film (i.e. Teflon ®, a fluorocarbon polymer) to make sample removal easier. This film, however, influences the measurement of the dielectric properties and limits the experimental temperature to a temperature less than the melting point of the Teflon ® release film. (Ceramic sensors with a gold conductor are used in single plate dielectric analyzers. See; Micromet product literature in the Information Disclosure Statement—Option S-60 dual function ceramic sensor for use in Micromet Eumetric System II microdielectrometer).

Accurate measurements of sample temperatures are also important since dielectric measurements are normally monitored as a function of temperature. In parallel plate dielectric analysis, typically a thermocouple is placed as close to the edge of the sample and plate as possible without contact, and the sample temperature is assumed to be that of the thermocouple (melting a sample on the thermocouple would require extensive clean up or disposal of the thermocouple after the experiment). Obviously, this temperature measurement is not as accurate as measuring the temperature of the sample directly. (In single plate dielectric analyzers it is known to incorporate a thermal diode in the electrode. See; Micromet product literature in the Information Disclosure Statement—Option S-1 integrated circuit dielectric sensor for use in the Micromet Eumetric System II microdielectrometer).

A parallel plate dielectric analyzer is needed which can vary the spacing between the electrodes as the sample expands, contracts, or melts in order to keep the electrodes in constant contact with the sample. As the electrode spacing is varied, the analyzer must also be able to sense the distance between them so that the dielectric calculations are accurate regardless of electrode spacing. A dielectric analyzer is needed which has electrodes which are easily replaced if their surfaces become marred. A dielectric analyzer is also needed which will give accurate temperature measurements of the sample.

Dielectric analysis using parallel plate electrodes is a powerful technique, however, it is primarily used to characterize the bulk properties of a material, in that the excitation signal is monitored through the entire thickness of the material. This constraint results in some critical limitations. Often times thick samples are of interest to be analyzed. In the parallel plate technique, the signal to noise ratio decreases as a function of increasing distance between the electrode plates. Larger plates could be uitlized to increase the area thereby increasing the signal however there does exist a practical limitation. Many times the surface of a material is to be analyzed. In polymer molding, skin effects are of interest due to faster cooling of the material's surface than its interior. The chemical and mechanical properties of the surface of the material are more indicative of its end use properties than the bulk properties. Coatings on a material surface are also of interest in dielectric analysis. Paints, adhesives, and copolymers often require analysis. A parallel plate measurement would detect the properties of the coating and its associated substrate in a bulk fashion. It is impossible to analyze surface characteristics by parallel plate analysis.

An alternate technique was developed and is commonly known which addresses the limitations of the parallel plate measurement. An interdigitated combed electrode is commonly used for obtaining dielectric measurements on surfaces of materials and fluids. Probes of this type have been used for many years as moisture detection devices. U.S. Pat. No. 3,696,360 to Gajewski, discloses an interdigited electrode for moisture sensing. In the past few years these interdigitated probe structures were adapted to measure dielectric properties of materials. See, *Society for the Advancement of Material and Process Engineering Journal*, Volume 19, No. 4, July/August, 1983. U.S. Pat. Nos. 4,710,550 and 4,723,908 both to Kranbuehl also disclose the use of single surface interdigitated pectinate electrodes for measurement of dielectric properties of materials. Another form of a single surface interdigitated dielectric sensor is disclosed in copending U.S. patent application Ser. No. 07/274,461 assigned to the assignee of the present invention.

In the single surface analysis technique a sample is placed on the electrode surface, an alternating electric voltage is applied to one "finger" or comb of the interdigitated fingers or combs of the electrode array, thereby inducing a current which passes through the sample and is measured at the other finger of the array. These two fingers are termed excitation and response electrodes respectively. In this fashion, the field only penetrates the surface of the material. The penetration depth of the alternating fields is approximately equal to the distance separating the fingers in the interdigitated electrode array. This technique is ideal for monitoring the dielectric characteristics of surfaces of materials as well as fluids, curing systems, adhesives, and relatively low viscosity materials.

Many limitations also arise when performing single surface dielectric analysis of materials. Most experiments require samples to be urged into contact with the electrode array by applying a constant force. As previously mentioned, the applied alternating field penetrates into the sample a finite distance. If the means to apply force to the sample penetrates this field area, accurate measurements are compromised. As with parallel plate analysis, samples are typically tested as a function of temperature. An analagous problem arises using single surface electrodes as with parallel plate electrodes. In a constant force experiment, at elevated temperatures, the sample begins to flow and the force application means drives toward the electrode array, penetrating the field area inducing severe errors into the dielectric measurement. As the temperature further increases the means for applying force to the sample eventually displaces all of the sample and rests entirely on the surface of the electrode array thereby terminating the experiment.

Due to the diversity of the two measurement techniques separate instruments have been required for single surface and parallel plate dielectric measurements until now.

A dielectric analyzer is needed which can apply and vary a force to a sample on a single surface electrode sensor and sense the distance between the electrode surface and the means for applying the force.

A dielectric analyzer is also needed which can perform dielectric analysis in both parallel plate and single surface modes within a single instrument.

SUMMARY OF THE INVENTION

Provided by this invention is an improved apparatus using parallel plate electrodes or single surface electrodes which measures the dielectric properties of a sample as a function of temperature having the following:

(a) a distance sensor for accurately measuring the varying distance between the electrodes (when used in the parallel plate mode), such as a linear voltage differential transformer (LVDT), and means responsive to the distance sensor for positioning the electrodes;

(b) a force transducer for measuring the applied force on the sample and means responsive to the force transducer to give a desired force by varying the electrode spacing;

(c) disposable electrodes made using thick film technology composed of a ceramic substrate with a conductor adhered to its surface; and (d) a temperature sensor built into one of the electrodes such as a metallic strip applied to the surface of one of the electrodes and means to measure the resistance across the metallic strip.

BRIEF DESCRIPTION OF THE DRAWINGS

FIG. 6 is an exploded perspective view depicting the single surface ram unit and the components therein.

FIG. 14 is a bottom plan view of the response electrode as viewed from the line 4—4 of FIG. 4.

FIG. 15 is a top plan view of the excitation electrode as seen from the line 5—5 of FIG. 4.

FIG. 16 is a sectional view of the response electrode taken on the line 6—6 of FIG. 14.

FIG. 17 is a sectional view of the excitation electrode taken on the line 7—7 of FIG. 15.

DETAILED DESCRIPTION OF THE PARALLEL PLATE SYSTEM

Figure 1:
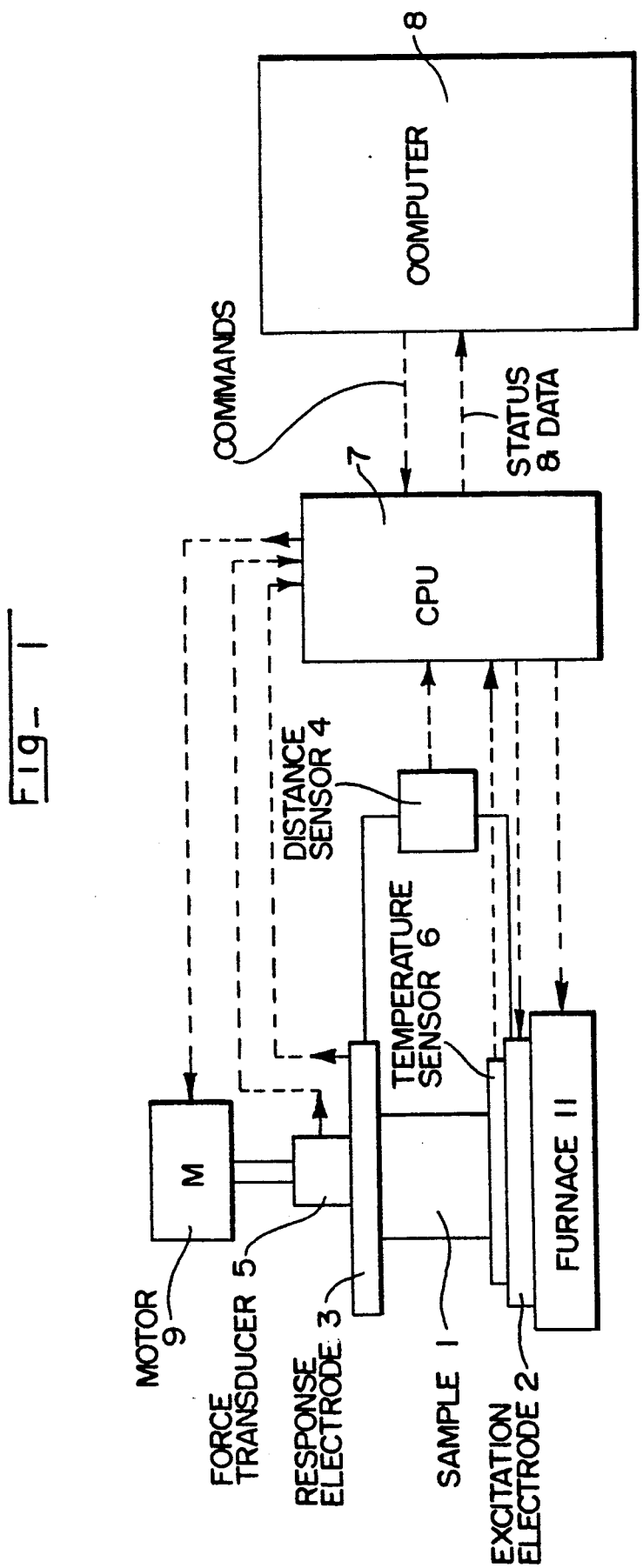
FIG. 1 is a schematic of the apparatus using parallel plate electrodes.

Referring now to the drawing in FIG. 1, the parallel plate dielectric analyzer includes stationary excitation electrode 2 and moveable response electrode 3 positioned above excitation electrode 2. The electrodes are positioned parallel to each other and adapted to receive sample 1 there between. An electrical signal is provided to excitation electrode 2. The electrical signal passes through sample 1 and into response electrode 3. The output signal from electrode 2 is then sent to central processing unit (CPU) 7.

Excitation electrode 2 is in contact with heating unit 11. In order to calculate dielectric properties as a function of temperature, heating unit 11 is used to vary the sample temperature. A thermal method is programmed into computer 8 which gives commands to CPU 7 which in turn controls heating unit 11. The sample temperature is measured by temperature sensor 6 which is applied to excitation electrode 2. The signal from temperature sensor 6 is sent to CPU 7 for a temperature calculation and this data is then sent to computer 8 for data storage and further analysis.

As the temperature of the sample changes, the sample thickness varies as a function of its CTE. This can vary the distance between the electrodes. Because the calculation of the sample's dielectric properties is dependent upon knowing the correct distance between the electrodes, the apparatus includes distance sensor 4 to measure the distance between the electrodes. The distance sensor sends a signal to CPU 7. CPU 7 uses the signal to calculate the distance between the electrodes. CPU 7 then uses this distance calculation in conjunction with the input signal to excitation electrode 2, the output signal from response electrode 3 and the surface area of response electrode 3 to calculate the dielectric properties of the sample. These data on the sample's dielectric properties are then sent to computer 8 for storage and data analysis.

In addition, computer 8 can be programmed to command CPU 7 to vary the electrode spacing by using motor 9 to raise or lower response electrode 3. This feature is critical to ensure that if a sample melts, the electrodes don't come in contact with each other and prematurely terminate the experiment.

In order to assure that the electrodes are in constant contact with the sample, the apparatus includes force transducer 5 which measures the force exerted on the sample by response electrode 3. Force transducer 5 sends a signal to CPU 7 where the signal is processed to provide the force on the sample. This data is then fed to computer 8. Computer 8 can be programmed to command CPU 7 to give a desired force on the sample by raising or lowering response electrode 3 using motor 9.

Under normal operating conditions computer 8 is programmed to command CPU 7 to run under some minimal constant force in order to assure that the electrodes are in contact with the sample as its thickness varies as a function of temperature. However, computer 8 can also be programmed so that an override of the constant force mode occurs at some minimum electrode spacing. This will assure that if the sample melts, the electrodes don't come in contact with each other and short out.

Description of the Single Surface System

Figure 1A:
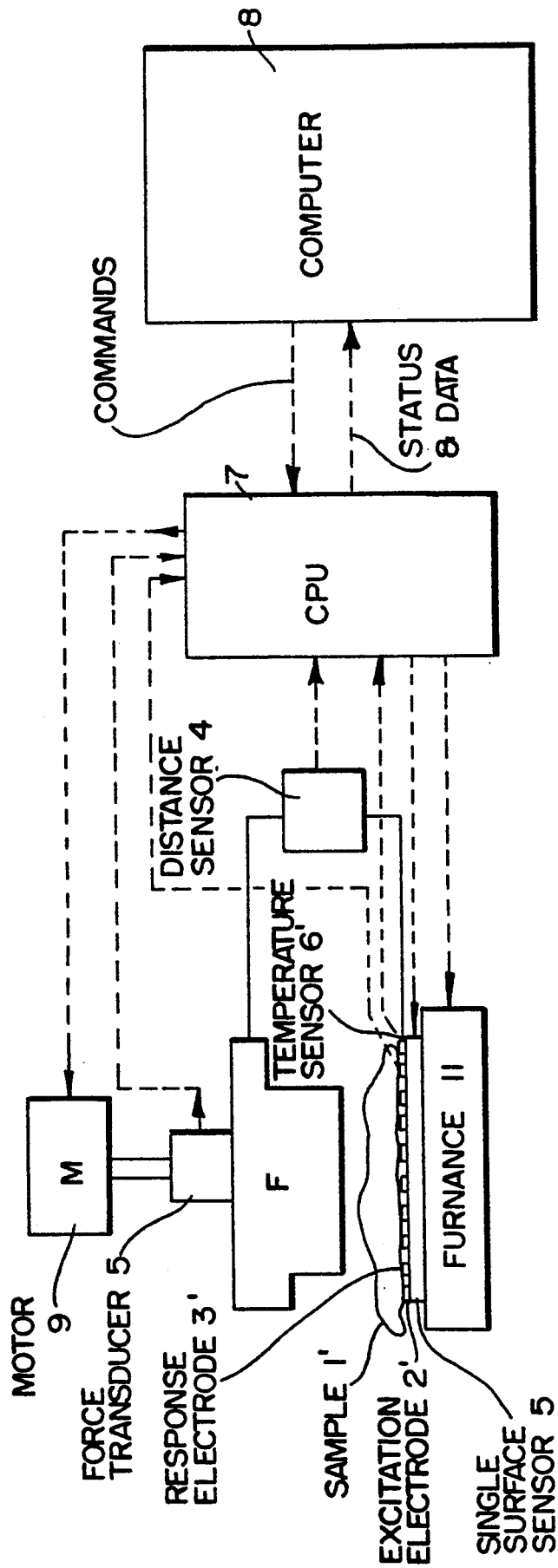
FIG. 1A is a schematic of the apparatus using a single surface sensor.

Referring now to the drawing in FIG. 1A, the single surface dielectric analysis system includes a single surface sensor S having an excitation electrode 2' and response electrode 3' on the upper surface thereof. A sample 1' is urged into contact with the single surface sensor S by force application means F.

An electrical signal is provided to excitation electrode 2' in the form of an alternating electric field which induces an alternating current. The alternating current passes through sample 1' into response electrode 3'. The output signal from response electrode 3' is then sent to CPU 7 where the amplitude and phase of the resultant alternating current is measured as it is acted upon by sample 1'. Single surface sensor S is in contact with heating unit 11.

In order to calculate dielectric properties as a function of temperature, heating unit 11 is used to vary the sample temperature. A thermal method is programmed into computer 8 which gives commands to CPU 7 which in turn controls heating unit 11. The sample temperature is measured by temperature sensor 6' which is applied to single surface sensor S. The signal from temperature sensor 6' is sent to CPU 7 for a temperature calculation and this data is then sent to computer 8 for data storage and further analysis.

In order to assure that sample 1' is in constant contact with the single surface sensor S, the apparatus includes force transducer 5 which measures the force exerted on the sample by force application means F. Force transducer 5 sends a signal to CPU 7 where the signal is processed to provide the force on the sample. These data are then fed to computer 8. Computer 8 can be programmed to command CPU 7 to give a desired force on the sample by raising or lowering force application means F using motor 9.

As the temperature of the sample changes, the sample thickness varies as a function of its CTE and applied force thereon. As the sample begins to melt due to increasing temperature, force application means F drives closer to the surface of single surface sensor S. It is important that the force application means F not penetrate into the alternating electric field which fringes above the excitation and response electrodes (See curves 314 in FIG. 19). To prevent this, the apparatus includes distance sensor 4 to measure the distance between the single surface sensor S and force application means F. The distance sensor sends a signal to CPU 7. CPU 7 uses the signal to calculate the distance between sensor S and force means F. Computer 8 can be programmed to command CPU 7 to vary the spacing by using motor 9 to raise or lower force application means F. This feature is critical to ensure that if a sample melts, the force application means F does not impinge the alternating electric field or come in to contact with the electrodes on the single surface sensor S and prematurely terminate the experiment.

Under normal operating conditions computer 8 is programmed to command CPU 7 to run under some constant force in order to assure that the electrodes are in contact with the sample as its thickness varies as a function of temperature. However, computer 8 can also be programmed so that an override of the constant force mode occurs at some minimum electrode spacing. This will assure that if the sample melts, the force application means F does not come in contact with the electrodes of sensor S.

Preferred Embodiment of the Parallel Plate Apparatus

Figure 2:
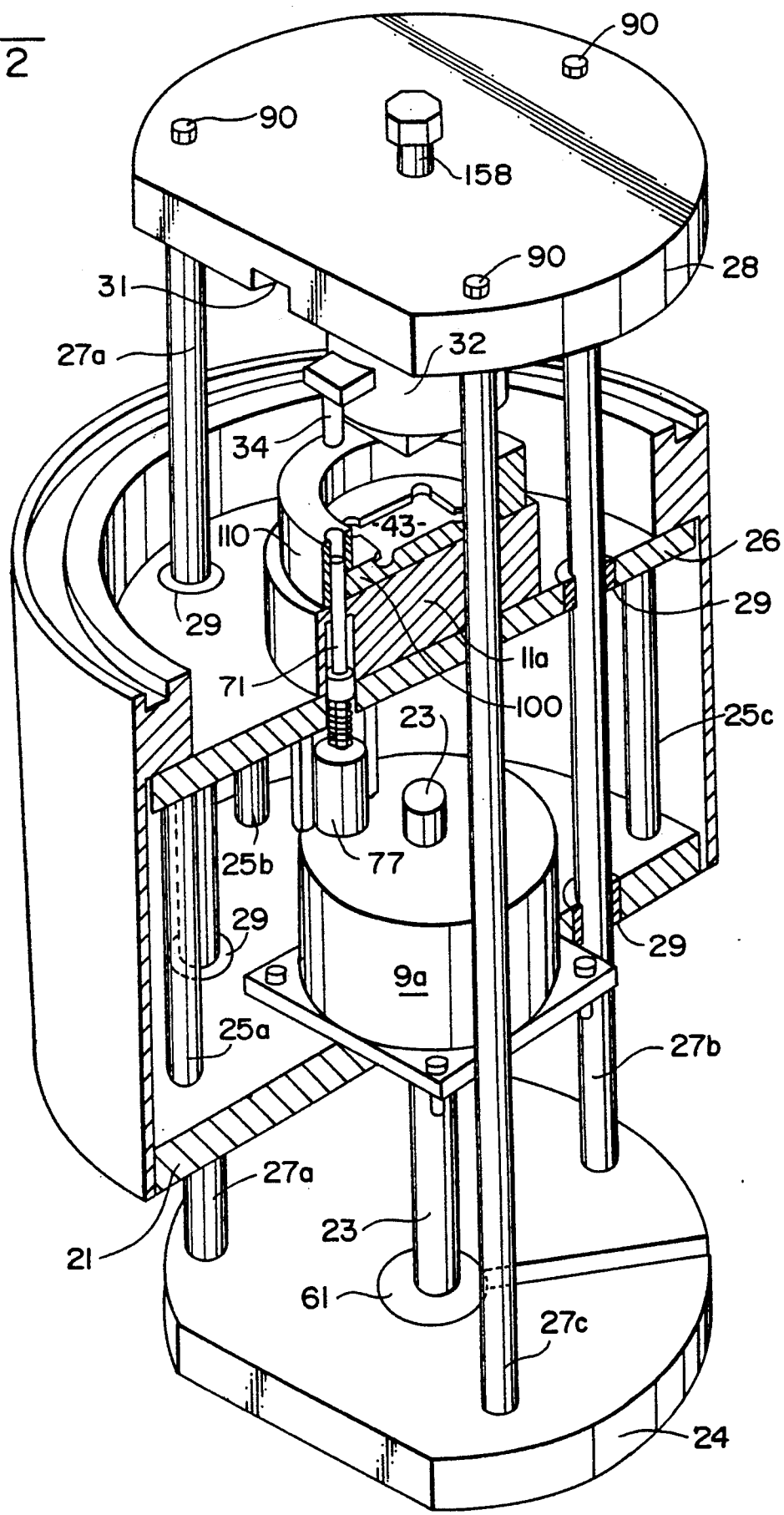
FIG. 2 is a perspective view of the apparatus with parts broken away to show the inside.

The preferred embodiment of the parallel plate dielectric measurement apparatus is shown in FIG 2. A disc shaped steel stationary base 21 lies in a horizontal plane and has three vertical steel columns 25a, 25b, and 25c of equal length attached to the upper surface of base 21. The columns are configured around the perimeter of base 21. The top of the steel columns are bolted to upper base 26 which is also a steel disc lying parallel to base 21.

Figure 11:
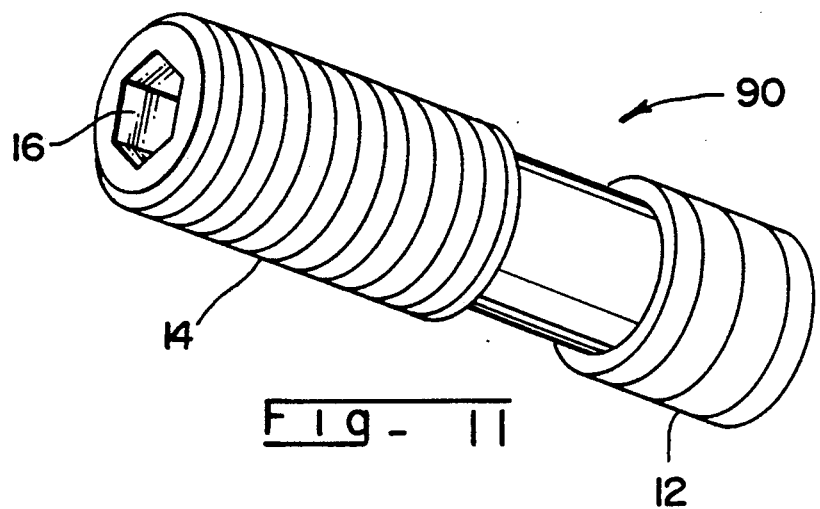
FIG. 11 is a perspective view of the parallelism adjustment screw used in the apparatus.
Figure 12:
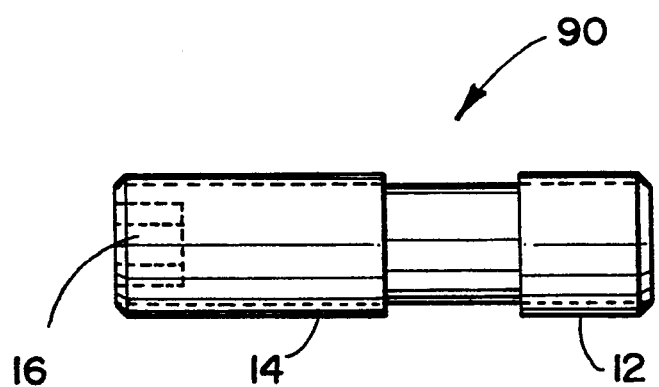
FIG. 12 is a side section view of the screw of FIG. 11.
Figure 13:
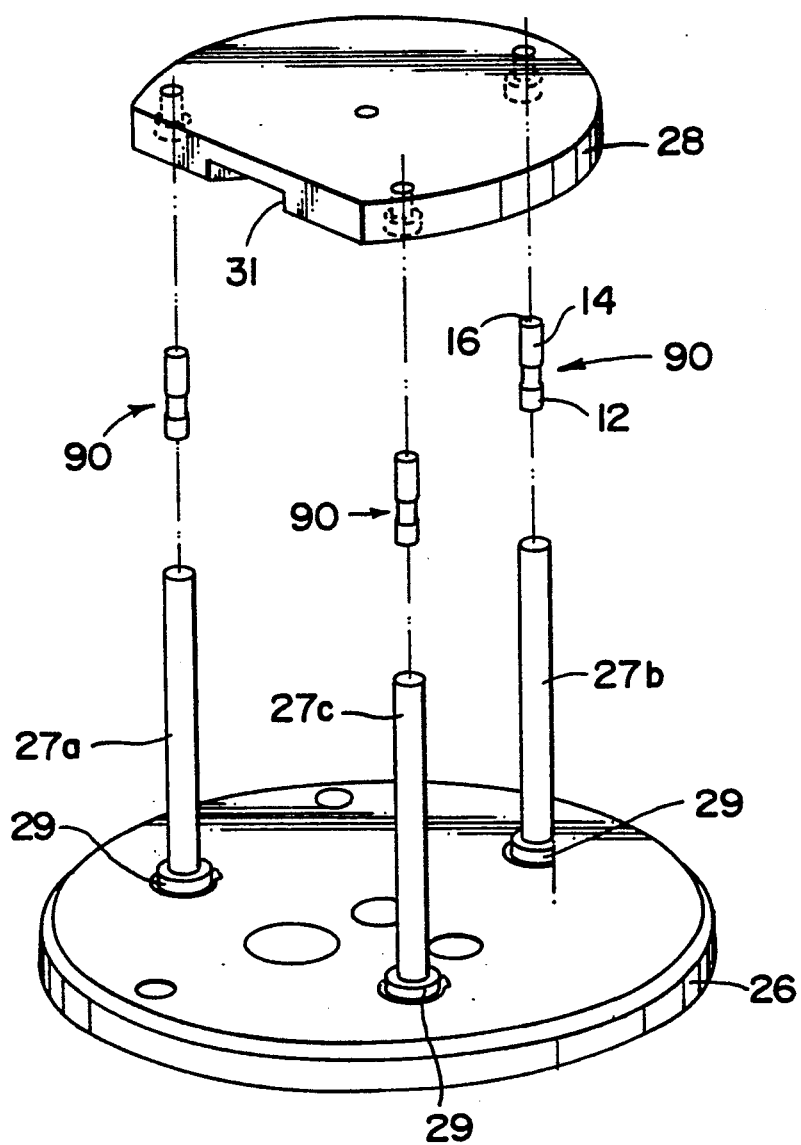
FIG. 13 is a perspective view of the apparatus depicting the location of the screw of FIGS. 11, 12.

Motor 9a is bolted to the upper surface of base 21. Positioned along the cylindrical axis of motor 9a is shaft 23 whose lower end is connected to plate 24, a steel disc. Numerous different types of motors can be used as will be apparent to one skilled in the art. In our preferred embodiment motor 9a is a permanent magnet stepping DC motor, EAD size 34, model number LA3-4AGK-9 manufactured by Eastern Air Devices. Plate 24 lies in a horizontal plane and has three vertical steel columns of equal length 27a, 27b and 27c bolted to its upper surface. The vertical steel columns pass through bearings 29 in base 21 and upper base 26. The top of columns 27a, 27b, and 27c are bolted to upper plate 28 which is a steel disc also lying in a parallel plane using adjustable compound-threaded screw 90. As shown in FIG. 11, one end 12 of the adjustment screw 90 is engagable with a coarse thread provided in the upper portion of the top of columns 27a, 27b, and 27c. The other end 14 of the adjustment screw is engagable with a fine thread provided in steel disc 28. The screws can be rotated by use of a simple Allen wrench engagable with the hex socket 16 provided in one end of the screw. FIG. 13 is an exploded perspective of the apparatus showing the position of the adjustment screw of FIG. 11. By individually rotating adjustment screws 90, upper plate 28 can be precisely positioned to lie in a parallel plane with respect to upper base 26.

As motor 9a operates, shaft 23 moves up or down thereby moving plate 24 and upper plate 28 up or down.

Figure 7:
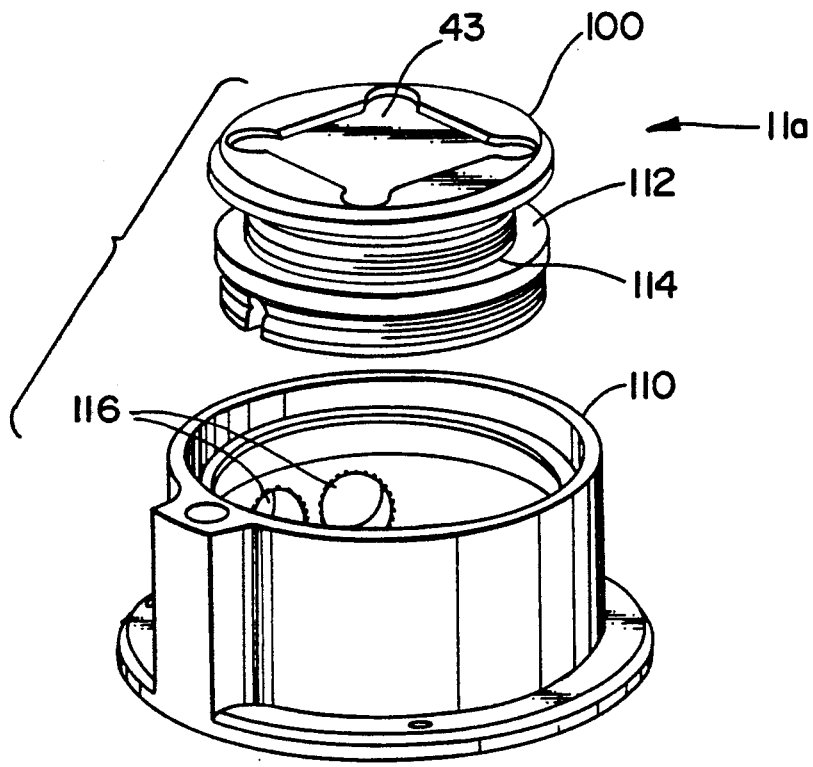
FIG. 7 is a perspective view of the furnace used in the apparatus which has been exploded to show the components therein.
Figure 8:
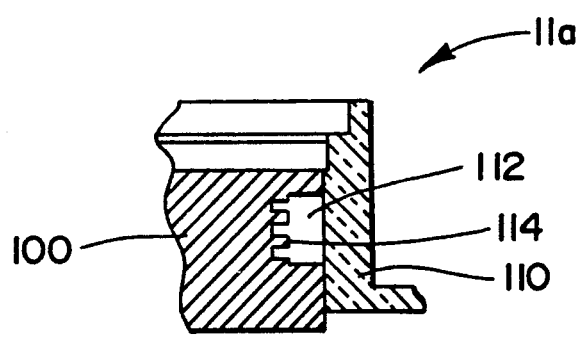
FIG. 8 is a side elevational view in section of the furnace shown in FIG. 7.
Figure 9:
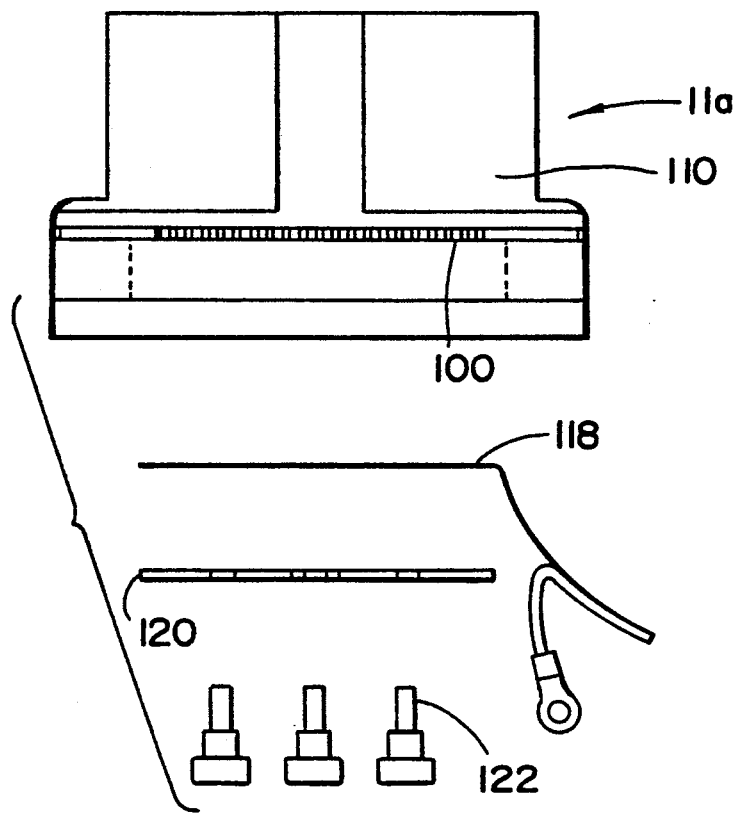
FIG. 9 is an exploded side elevational view depicting the used in the furnace of FIG. 7.
Figure 10:
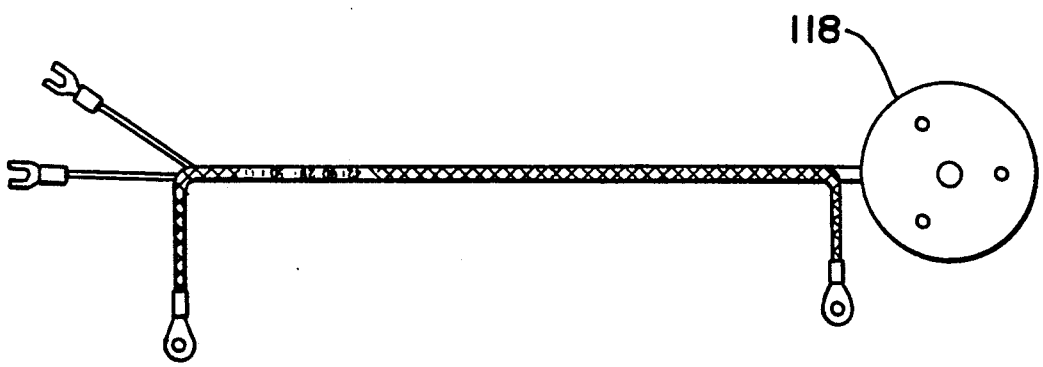
FIG. 10 is a plan view of the heating element shown in FIG. 8.

Attached to the upper surface of upper base 26 is heating unit 11a. Referring to FIG. 7 heating unit 11a is used to heat the sample and consists of a cylindrical heat sink 100 which is brazed in a position in the interior of cooling ring 110. The heat sink is preferrably machined from silver and has a channel 112 around its periphery. The interior wall of channel 112 is provided with grooves 114. The grooves serve to increase the surface area of the heat sink 100 in channel 112. A cooling ring 110, preferably machined from brass is placed around the circumference of the heat sink 100 and brazed in place. The cooling ring 110 contains two ports 116 for allowing coolant to be introduced into channel 112. FIG. 8 shows a section of heating unit 11a after the brazing process is complete. As can be seen, liquid coolant can be circulated through channel 112. The increased surface area provided by grooves 114 allow for more effective heat transfer from the liquid coolant to heat sink 100. A mica clad inconel heater 118 is bolted to the undersurface of heat sink 100 as shown in FIG. 9. Backing plate 120 serves to support heating element 118 firmly against heat sink 100 using bolts 122. A plan view of heating element 118 is shown in FIG. 10. The material used to form heat sink 100 must have a higher thermal conductivity than that of cooling ring 110. This allows the heat generated by heating element 118 to be preferentially absorbed by heat sink 100 as opposed to cooling ring 110.

Referring back to FIG. 7 heat sink 100 has an indentation 43 in the upper surface which is sized to receive either a single surface dielectric sensor S' (see FIG. 18) or excitation electrode 2a of the parallel plate system.

Figure 3:
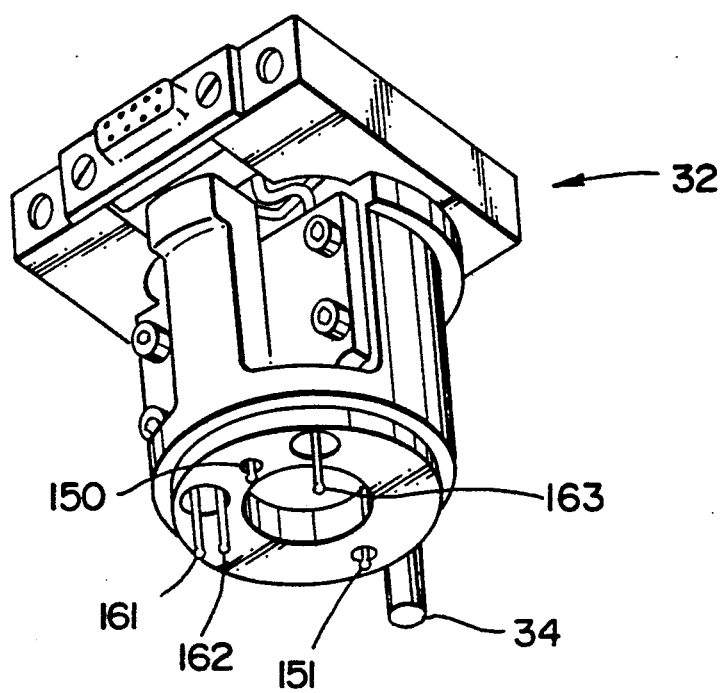
FIG. 3 is a perspective view of the parallel plate ram unit used in the apparatus.
Figure 5:
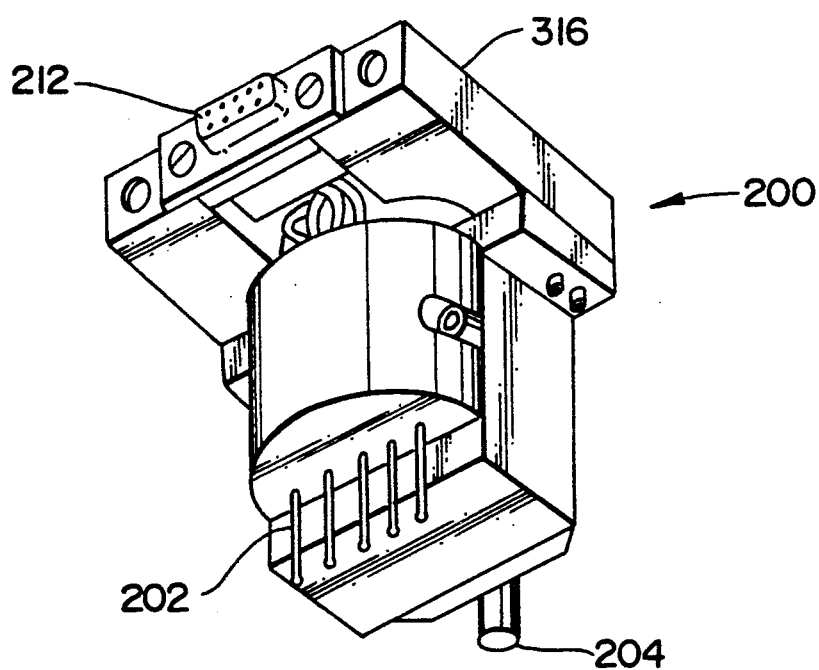
FIG. 5 is a perspective view of the single surface ram unit used in the apparatus.

As shown in FIG. 2 the bottom surface of upper plate 28 contains channel 31 fitted to slidably accept a ram unit of the single surface or parallel plate type as shown in FIGS. 5 and 3 respectively. The single surface system will be described in the next section. Parallel plate ram unit 32 is a housing designed to detachably hold response electrode 3a. Parallel plate ram unit 32 should be made of a high thermal insulator which is also not electrically conductive. Preferably parallel plate ram unit 32 is made of ceramic. Parallel plate ram unit 32 also contains the electrical contacts for excitation electrode 2a, response electrode 3a, and the temperature sensor. Attached to the side of parallel plate ram unit 32 and extending outwardly and then downwardly is vertical plunger 34. Parallel plate ram unit 32 is discussed in more detail below.

Means to determine the distance between response electrode 3a and excitation electrode 2a is provided Cooling ring 110, heating unit 11a and upper base 26 contain cavities sized and positioned such that linear voltage differential transformer (LVDT) 77 is placed directly beneath plunger 34. As parallel plate ram unit 32 is lowered into position such that response electrode 3a is in contact with the sample, plunger 34 depresses spring loaded steel rod 71 which is attached to the core of LVDT 77. LVDT 77 operates in the same manner as LVDTs well known in the prior art. Spring loaded steel rod 71 is depressed by plunger 34 and the core moves through the LVDT coil which is positionally fixed in relation to the moving core. This allows very precise and accurate determination of the distance between the response and excitation electrodes. The LVDT in our preferred embodiment is of the type TRANS TEK AC-AC #0291-0000 manufactured by Trans-Tek Inc.

Plate 24 includes force transducer 61. There are numerous types of force transducers known to one skilled in the art which will work in this application. In our preferred embodiment the force transducer includes two steel blocks which clamp the ends of two solid state strain gauge force translators of the type Revere Model FT30-40. The other ends of both force sensors are clamped in a block which is rigidly fixed to the end of motor shaft 23. This arrangement allows precise and accurate measurement of the force motor 9a applies to plate 24. As parallel plate ram unit 32 comes in contact with the sample, the force measured is equal to the force applied to the sample.

Detachably connected to the underside of parallel plate ram unit 32 is response electrode 3a. Response electrode 3a (see FIGS. 14 and 16) comprises a thin square ceramic wafer substrate 33 with a thin round layer of gold conductor 51 applied to its surface. Guard ring 52 surrounds gold conductor 51. Guard ring 52 is a second thin circular, concentric layer of gold applied to ceramic substrate 33 which essentially surrounds but is not in contact with 51. (Guard rings are well known in the art and are used to assure that the signal received by the response electrode is unaffected by fringing fields.) Response electrode 3a has two gold plated holes 53a and 53b running completely through the ceramic wafer in opposing corners of the square. These gold plated holes are used as both electrical contacts and as receptors for mechanical grips used to hold response electrode 3a in place. Gold plated hole 53a is in electrical contact with gold conductor 51 through thin gold strip 55. Guard ring 52 is "broken" around gold strip 55 so that there is no electrical connection between gold conductor 51 and guard ring 52. Gold plated hole 53b intersects guard ring 52 and they, therefore, are also in electrical contact.

Excitation electrode 2a (see FIGS. 15 and 17) is a thin square ceramic wafer 101 with a thin round gold layer 102 applied to its surface. Excitation electrode 2a sits in indentation 43 of heat sink 100 with gold conductor 102 facing up. Thus, excitation electrode 2a is easily put into place or removed. Gold conductor 102 is in electrical contact with contact point 103 through gold strip 107. Also applied to the surface of ceramic wafer 101 is metallic strip 104, preferably platinum, running in a semicircle around the outside of gold conductor 102 but not in contact with gold conductor 102. At the end points of metallic strip 104 are electrical contact points 105a and 105b. Metallic strip 104 serves as a resistance temperature device. It is a well-known principal that by measuring the resistance of a metal, the temperature of the metal can be determined. Since metallic strip 104 is in direct contact with the sample, this gives a very accurate temperature reading of the sample.

Both the excitation and response electrodes can be manufactured using thick film hybrid technology (screen printed conductor layers) well known to those skilled in the art.

Figure 4:
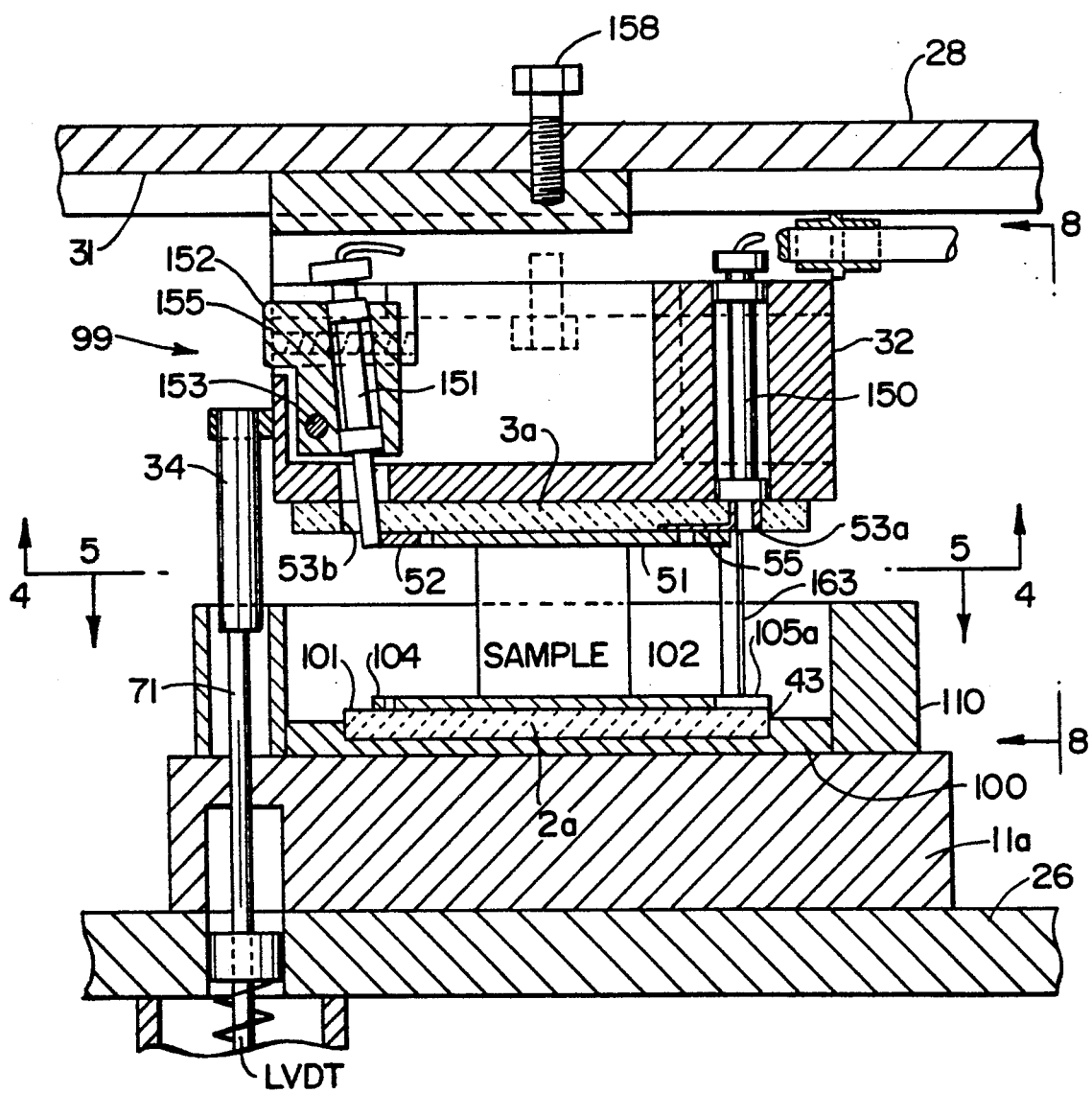
FIG. 4 is an enlarged fragmentary vertical sectional view of the ram unit of FIG. 3.

FIG. 4 shows a cross section of upper plate 28, parallel plate ram unit 32, response electrode 3a, the sample, excitation electrode 2a, heat sink 100, furnace 11a and upper base 26. Excitation electrode 2a is seated in indentation 43 of heat sink 100. The sample is placed on the upper surface of excitation electrode 2a. Response electrode 3a is in contact with the upper surface of the sample and is detachably attached to parallel plate ram unit 32.

Attachment and detachment of response electrode 3a to parallel plate ram unit 32 is accomplished using stationary pin 150 and movable pin 151. These pins serve as both mechanical grips and electrical contacts. The pins are sized and spaced such that they fit into gold plated holes 53a and 53b of response electrode 3a. Pin 150 goes in hole 53a and pin 151 goes in hole 53b. Stationary pin 150 is seated in a cavity in parallel plate ram unit 32. Moveable pin 151 is seated in rotating housing 152 which is pivotally attached to parallel plate ram unit 32 by means of pivot screws 153. Only one of the pivot screws is visible in FIG. 4. Rotating housing 152 contains spring plunger 155 applying a counterclockwise force to the rotating housing around pivot screws 153. This in turn exerts a counterclockwise force on pin 151 which grips the interior surface of hole 53b and holds response electrode 3a into place. To release response electrode 3a, pressure is exerted on the upper exposed portion of rotating housing 152 as shown by arrow 99. This counteracts the force exerted by spring plunger 155, and causes rotating housing 152 and pin 151 to rotate clockwise. This rotation of pin 151 allows response electrode 3a to be slipped off of pin 150 and pin 151.

Figure 20:
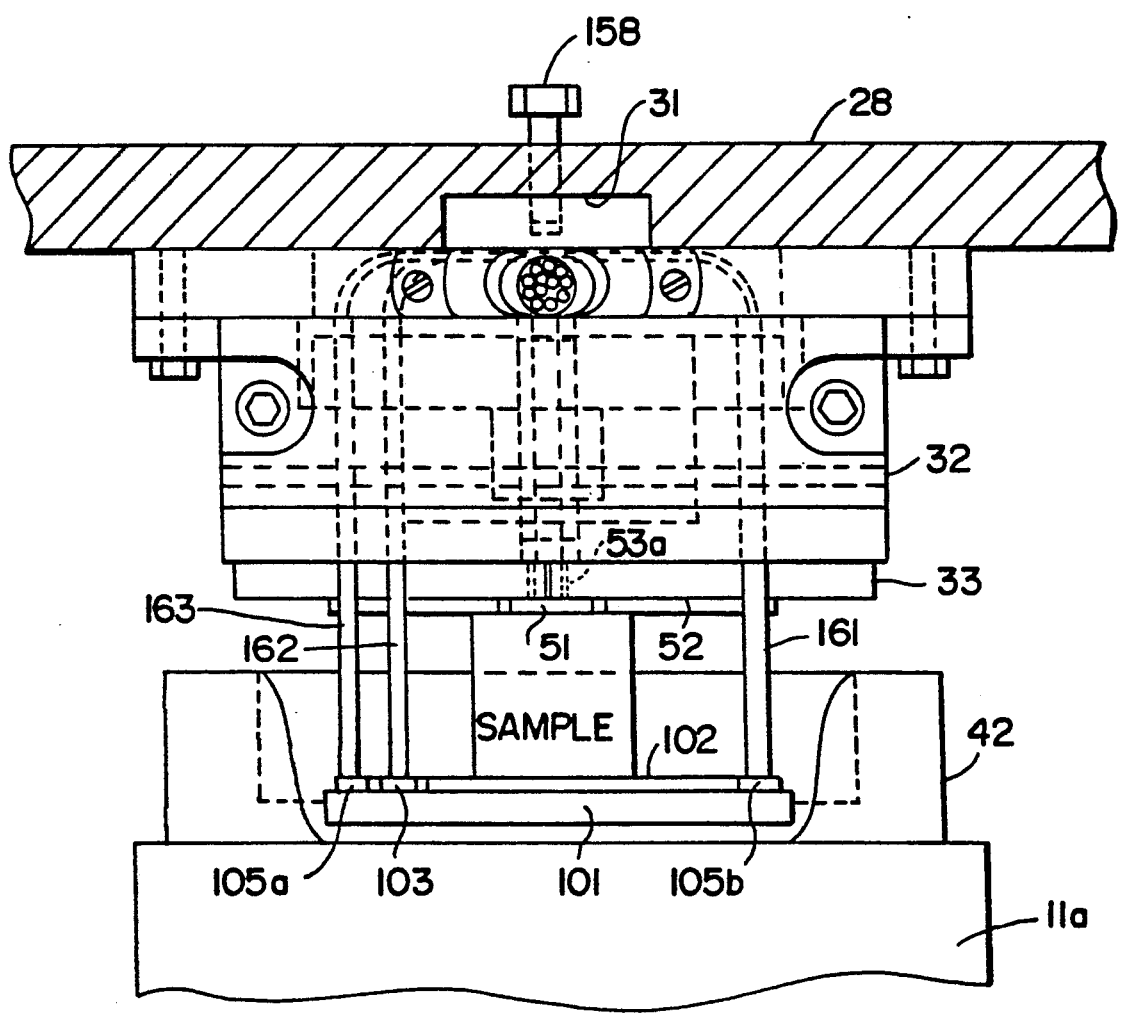
FIG. 20 is a fragmentory elevational view of the apparatus of FIG. 4 as seen from the plane 8—8 of FIG. 4 and with the proximate wall of block 42 broken away to better show the structure there behind.

Excitation electrode 2a (shown in FIGS. 15 and 17) sits in indentation 43 of heat sink 100. The electrical signals needed to excite conductor 102 and measure the resistance across platinum strip 104 are received from electrical contact pins 161, 162, and 163 as shown in FIG. 20. Only pin 163 is visible in FIG. 4. These pins are spring loaded electrical contact pins which are seated in the ceramic housing of parallel plate ram unit 32. These electrical contact pins are sping loaded to extend and retract approximately 0.25 inches. This allows the parallel plate ram unit 32 to move up and down in a vertical direction with respect to excitation electrode 2a while maintaining electrical contact therewith. This allows for a sample to expand and contract during an experiment without sacrificing electrical contact. This feature also allows samples having varying thicknesses to be analyzed. Use of these electrical contact pins also eliminate the need to solder wires to the electrodes. Typically solders will melt at temperatures desired for dielectric analysis resulting in loss of electrical contact. Pins 161, 162 and 163 are positioned so that as parallel plate ram unit 32 is lowered the pins contact their respective electrical contact points 105a, 105b and 103 on the surface of excitation electrode 2a. Pin 161 is in contact with electrical contact point 105b, pin 162 is in contact with electrical contact point 103 and pin 163 is in contact with electrical contact point 105a.

Operation of the Parallel Plate System

Initially parallel plate ram unit 32 is decoupled from the instrument. The response electrode is attached to parallel plate ram unit 32 by slipping pins 150 and 151 through holes 53a and 53b when rotating housing 152 is pressured such that it has rotated clockwise (as shown in FIG. 4). Releasing the spring loaded rotating housing 152 "grips" response electrode 3a and holds it in place with gold conductor 51 facing down. Parallel plate ram unit 32 is then affixed to upper plate 28 by sliding ram unit 32 into channel 31. Parallel plate ram unit 32 is then captured rigidly by tightening thumbscrew 158. Excitation electrode 2a is placed in indentation 43 in heat sink 100 with gold conductor 102 and platinum RTD 104 facing up.

At this point, calibration is begun. Motor 9a begins to drive, bringing parallel plate ram unit 32 toward excitation electrode 2a. Electrical contact pins 161, 162 and 163 make electrical connection with electrical contact points 105b, 103, and 105a, respectively. Motor 9a continues to drive until electrodes 2a and 3a are in contact with each other. LVDT calibration is set to 0.0 millimeters at this point. Motor 9a reverses direction and parallel plate ram unit 32 travels upward to remove all mechanical backlash from the system. An LVDT reading is taken at this point then parallel plate ram unit 32 travels upward again as a predetermined number of motor steps are being counted. Another LVDT calibration reading is then taken. By knowing the pitch of the motor lead screw and the number of steps driven, the theoretical distance traveled can be calculated. A two point calibration of the LVDT has been completed and stored in CPU 7.

Knowing the gain of the LVDT, motor 9a drives parallel plate ram unit 32 down to a selected distance between the electrodes. Now a sinusoidal voltage is applied to excitation electrode 2a. The resulting current is monitored at response electrode 3a. Knowing the dielectric properties of dry air, the electrodes are calibrated for dielectric measurements. Concurrently, the resistance of platinum strip 104 is being measured and calibrated. (Knowing the temperature of the furnace block via a thermocouple embedded within it, the RTD is calibrated to the thermocouple temperature). After all calibration values are stored, parallel plate ram unit 32 moves to full open position. A sample of interest is then placed on the excitation electrode 2a. A constant force or spacing experiment is selected. Threshold values (minimum/maximum) are determined and programmed into computer 8. A thermal method is programmed into computer 8. The experiment is ready to begin.

Parallel plate ram unit 32 then moves to the selected force or spacing and begins measuring the capacitance of the sample concurrent with the thermal method of heating unit 11a. As the experiment progresses, CPU 7 dynamically monitors force and spacing and drives motor 9a accordingly to maintain operator selected parameters.

By measuring capacitance, the permittivity of the sample (e') can easily be calculated using the following equation:

$$C = e_o e' A/d$$

where
  C = Capacitance
  $e_o$ 32 Permittivity of Free Space (a constant)
  e' = Permittivity of Sample (being measured)
  A = Area of Parallel Plate Response Electrode
  d = Distance Between the Excitation and Response Electrode Plates Preferred Embodiment of the Single Surface System The preferred embodiment of the single surface dielectric analysis system is essentially identical to the parallel plate system with the exceptions of the ram unit and type of electrode sensor used. Referring to FIG. 2 as previously mentioned, the bottom surface of upper plate 28 contains channel 31 fitted to slideably accept a ram unit of either the parallel plate (FIG. 3) or single surface (FIG. 5) type. The sliding fit in channel 31 along with thumbscrew 158 provides immediate interchangeability between the two types of ram units. A perspective view of the ram unit 200 used for the single surface measurement is shown in FIG. 5. Single surface ram unit 200 is a housing designed to apply force to a sample during a single surface dielectric experiment. Single surface ram unit 200 should be made of a high thermal insulator which is also not electrically conductive. Preferably ram unit 200 is made of ceramic. Single surface ram unit 200 also contains the electrical contacts 202 for a typical single surface dielectric sensor. Attached to the side of ram unit 200 and extending outwardly and then downwardly is vertical plunger 204. Single surface ram unit 200 is discussed in more detail below.

Figure 18:
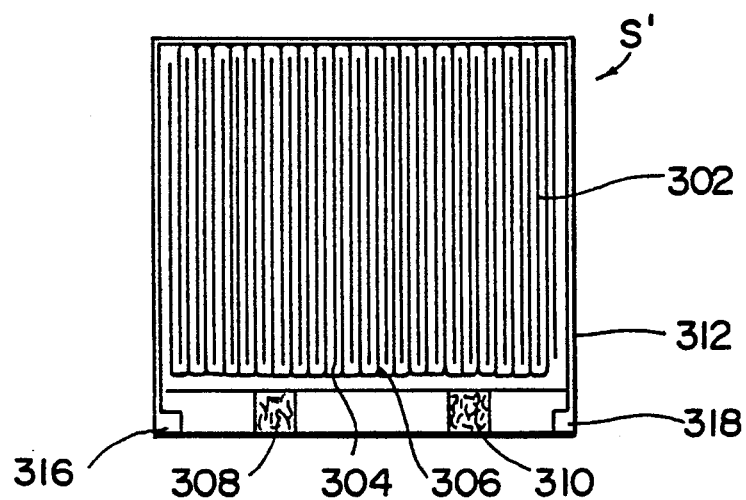
FIG. 18 is a top plan view of a single surface interdigitated dielectric sensor.
Figure 19:
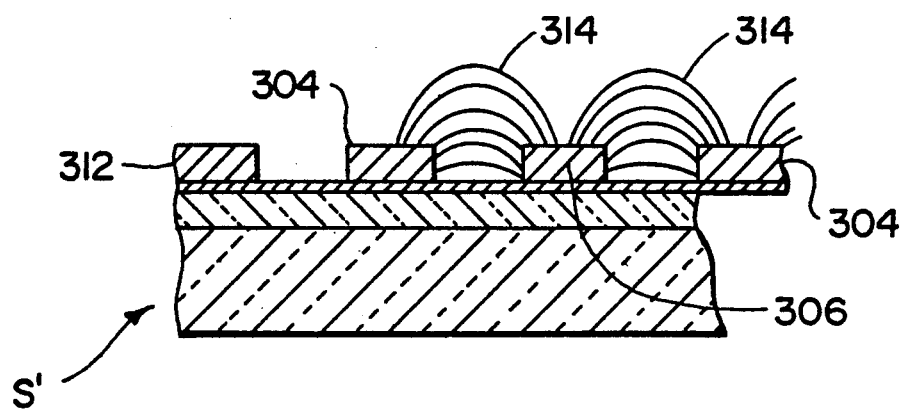
FIG. 19 is a side elevational view of the sensor of FIG. 18.

A top plan view of a single surface interdigitated electrode dielectric sensor S' is shown in FIG. 18. Sensor S' has an interdigitated electrode array 302 on its upper surface. Electrode array 302 consists of response electrode 304 and excitation electrode 306. Electrodes 304 and 306 terminate at electrical contact pads 308 and 310 respectively. Sensor S' may also contain a temperature sensor 312 on its surface. Contact pads 316 and 318 serve as electrical contacts for temperature sensor 312. Preferably temperature sensor 312 is a platinum RTD. A partial side section of sensor S' is shown in FIG. 19. Lines 314 represent the location of "fringing electrical fields" which penetrate the surface of a sample under analysis.

An exploded detailed perspective view of the single surface ram unit 200 is shown in FIG. 6. As shown, ram unit 200 contains a slide block 316 which slidably engages channel 31 previously shown in FIG. 2. Ram unit 200 also has a vertical plunger 204 bolted to flange 206 for engaging the LVDT system. Electrical contact pins 202 are provided in disengageable sockets 210. Pins 202 are spring loaded electrical contacts as described in the parallel plate section.

In the event of contamination by samples, pins 202 are easily removed from sockets 210 and discarded. A new set of pins 202 can then be inserted into sockets 210 facilitating a new experiment. Connector 212 provides the electrical connection from ram unit 200 to the main circuitry of the apparatus.

Means to determine the distance between single surface ram unit 200 and single surface sensor S' is identical to the means described in the parallel plate system where the vertical plunger 204 of ram unit 200 serves to enable LVDT to accurately measure the mentioned distance. Means for determining the force applied to the sample by the single surface ram unit 200 is also using the strain gage force measuring arrangement as described in the parallel plate section.

Operation of the Single Surface System

Single surface ram unit 200 is affixed to upper plate 28 by sliding ram unit 200 into channel 31. Ram unit 200 is then captured rigidly by tightening thumbscrew 158. Single surface sensor S' of the type shown in FIG. 18 is then placed in indentation 43 in heat sink 100 with the electrode array 302 and temperature sensor 312 facing ram unit 200.

At this point, calibration is begun. Motor 9a begins to drive, bringing ram unit 200 toward single surface sensor S'. Electrical contact pins 202 make electrical connection with electrical contact pads 308, 310, 316, and 318 respectively. Motor 9a continues to drive until sensor S' and ram unit 200 are in contact with each other. LVDT calibration is set to 0.0 millimeters at this point. Motor 9a reverses direction and ram unit 200 travels upward to remove all mechanical backlash from the system. An LVDT reading is taken at this point then ram unit 200 travels upward again as a predetermined number of motor steps are being counted. Another LVDT calibration reading is then taken. By knowing the pitch of the motor lead screw and the number of steps driven, the theoretical distance traveled can be calculated. A two point calibration of the LVDT has been completed and stored in computer 8.

Knowing the gain of the LVDT, motor 9a drives ram unit 200 down to a selected distance above the sensor S'. This distance is selected to be greater than the height of the fringing electric fields 314 (see FIG. 19) above sensor S'. Now a sinusoidal voltage is applied to excitation electrode 306. The resulting current is monitored at response electrode 304. Knowing the dielectric properties of dry air, the sensor is calibrated for dielectric measurements. Concurrently, the resistance of platinum strip 312 is being measured and calibrated. (Knowing the temperature of the furnace block via a thermocouple embedded within it, the RTD is calibrated to the thermocouple temperature). After all calibration values are stored, ram unit 200 moves to full open position. A sample of interest is then placed on sensor S'. A constant force or spacing experiment is selected. Threshold values (minimum/maximum) are determined and programmed into computer 8. A thermal method is programmed into computer 8. The experiment is ready to begin.

Ram unit 200 then moves to the selected force or spacing and begins measuring the capacitance of the sample concurrent with the thermal method of heating unit 11a. As the experiment progresses, CPU 7 dynamically monitors force and spacing and drives motor 9a accordingly to maintain operator selected parameters.

By measuring capacitance, the permittivity of the sample (e') can easily be calculated using the algorithms typically used in single surface dielectric measurements.

We claim:

1. A method of analyzing dielectric properties of a material, using a single surface sensor with interdigitated pectinate excitation and response electrodes thereon, comprising the following.
    (a) using a force application means to apply a force to a material under test to force the material into intimate contact with the electrodes of the sensor;
    (b) providing an alternating current electrical signal to the excitation electrode of the sensor that generates an alternating electric field in the material under test above the excitation and response electrodes;
    (c) detecting and measuring the amplitude and phase of an electrical response signal detected by the response electrode;
    (d) monitoring the force applied to the material under test using a force transducer;
    (e) monitoring the distance between the force application means and the single surface sensor; and
    (f) adjusting the force exerted by the force application means to ensure that the force application means does not penetrate the alternating electric field generated by the excitation electrode.

2. The method of claim 1 wherein the sensor and the material under test are in a temperature controllable environment and wherein the dielectric analysis is conducted as a function of temperature.

3. The method of claim 1 where the force on the material is controllable to provide various levels of force on the material.

4. The method of claim 1 where the thickness of the sample can be varied by controlling the force.

5. The method of claim 1 where the alternating current electrical signal is introduced to the sensor through spring loaded electrical contact pins.

6. The method of claim 2 wherein the temperature controllable environment is comprised of a heating element, a heat sink formed from a metal having a thermal conductivity, and a cooling ring formed from a metal having a lower thermal conductivity than the thermal conductivity of the heat sink.

7. The method of claim 6, wherein the heating element comprises a mica clad inconel heater.

8. In an apparatus for measuring the dielectric properties of a sample, the apparatus including a dielectric sensor comprising excitation and response electrodes, a temperature sensor adapted to sense the temperature of the sample, means for applying an input alternating current electrical signal to the excitation electrode, and means connected to the response electrode for providing an output signal; wherein the input alternating current electrical signal to the excitation electrode generates an electrical field in the sample and an alternating current signal in the response electrode, the improvements which comprise:
    means for applying a force to the sample;
    means for monitoring the distance from the means for applying the force to the surface of the sensor; and
    means for adjusting the force applied to the sample to ensure that the means for applying the force does not penetrate the alternating electric field generated by the excitation electrode.

9. The apparatus for measuring the dielectric properties of a sample of claim 8, further comprising a spring loaded alternating current electrical contact pin for inputting the input electrical signal to the excitation electrode.

* * * * *